United States Patent
Wang (10) Patent No.: US 11,052,197 B2
(45) Date of Patent: Jul. 6, 2021

(54) PREFILLED INJECTION PEN

(71) Applicant: BEIJING GANGAN TECHNOLOGY CO., LTD., Beijing (CN)

(72) Inventor: Chunsheng Wang, Beijing (CN)

(73) Assignee: BEIJING GANGAN TECHNOLOGY CO., LTD., Beijing (CN)

( * ) Notice: Subject to any disclaimer, the term of this patent is extended or adjusted under 35 U.S.C. 154(b) by 289 days.

(21) Appl. No.: 16/095,349

(22) PCT Filed: Apr. 20, 2017

(86) PCT No.: PCT/CN2017/081254
§ 371 (c)(1),
(2) Date: Oct. 20, 2018

(87) PCT Pub. No.: WO2017/181967
PCT Pub. Date: Oct. 26, 2017

(65) Prior Publication Data
US 2019/0125977 A1    May 2, 2019

(30) Foreign Application Priority Data

Apr. 21, 2016 (CN) .................. 201610258059.X (51) Int. Cl.
*A61M 5/315* (2006.01)
*A61M 5/31* (2006.01)
*A61M 5/24* (2006.01)
*A61M 5/20* (2006.01)

(52) U.S. Cl.
CPC ...... *A61M 5/31551* (2013.01); *A61M 5/3129* (2013.01); *A61M 5/3155* (2013.01);
(Continued)

(58) Field of Classification Search
CPC ............ A61M 5/31551; A61M 5/3155; A61M 5/31583; A61M 5/31585; A61M 5/31586;
(Continued)

(56) References Cited

U.S. PATENT DOCUMENTS 7,169,132 B2    1/2007  Bendek et al.
2006/0247581 A1* 11/2006  Pedersen ........... A61M 5/31541
                                                604/218
(Continued)

FOREIGN PATENT DOCUMENTS

CN          1723054 A     1/2006
CN        101829381 A     9/2010
(Continued)

OTHER PUBLICATIONS

International Search Report of PCT Patent Application No. PCT/CN2017/081254 dated Jun. 23, 2017.
(Continued)

*Primary Examiner* — Bhisma Mehta
*Assistant Examiner* — John J Crawford (57) ABSTRACT

A prefilled injection pen for injecting insulin, the prefilled injection pen including: a screw rod, a memory connection barrel, a fixed barrel and a rotating barrel. A plurality of first one-way teeth is evenly distributed on an end surface of the rotating barrel. The memory connection barrel is disposed inside the rotating barrel. The inner wall of the memory connection barrel is provided with a protrusion matching a thread of the screw rod. An end face of one end of the fixed barrel is provided with a ratchet pawl matching the first one-way teeth. The fixed barrel is also provided with a first inner thread matching the screw rod. The screw rod is provided with two machined plane surfaces. A plunger is disposed at one end of the screw rod and a stopper is disposed in a thread groove at the other end of the screw rod.

8 Claims, 7 Drawing Sheets

(52) U.S. Cl.
CPC .... *A61M 5/31541* (2013.01); *A61M 5/31583* (2013.01); *A61M 5/31585* (2013.01); *A61M 5/31593* (2013.01); *A61M 5/2033* (2013.01); *A61M 5/31528* (2013.01); *A61M 2005/2407* (2013.01)

(58) Field of Classification Search
CPC .......... A61M 5/31528; A61M 5/31541; A61M 5/31553; A61M 5/31545; A61M 5/31548; A61M 5/31576; A61M 5/31563; A61M 5/3129; A61M 5/2033; A61M 2005/2407; A61M 5/31595
See application file for complete search history.

(56) References Cited

U.S. PATENT DOCUMENTS

2015/0018771 A1  1/2015  Schenker et al.
2015/0314076 A1  11/2015 Markussen

FOREIGN PATENT DOCUMENTS

| CN | 102716529 A | 10/2012 | |
|---|---|---|---|
| CN | 104321096 A | 1/2015 | |
| CN | 105749383 A | 7/2016 | |
| CN | 205759066 U | 12/2016 | |
| EP | 2829292 A1 | 1/2015 | |
| WO | 20070060156 A1 | 5/2007 | |
| WO | 20130137893 A1 | 9/2013 | |
| WO | WO-2013137893 A1 * | 9/2013 | ........ A61M 5/31593 |
| WO | 2015032780 A1 | 3/2015 | |
| WO | 2016055623 A1 | 4/2016 | |

OTHER PUBLICATIONS

First Office Action of Counterpart Chinese Patent Application No. 201610258059.X dated Oct. 11, 2016.
Examination Report of Counterpart European Patent Application No. 17785451.0 dated Jul. 19, 2019.

* cited by examiner

PREFILLED INJECTION PEN

The present disclosure claims the priority to the Chinese patent application with the filing No. CN201610258059.X, filed on Apr. 21, 2016 with the China National Intellectual Property Administration (CNIPA) of the People's Republic of China, entitled "Prefilled injection pen", which is incorporated herein by reference in its entirety.

TECHNICAL FIELD

The present disclosure relates to the technical field of insulin injection for diabetics, and particularly to a prefilled injection pen (pen-shaped prefilled injector).

BACKGROUND ART

Diabetes is a group of metabolic disorders featured by high blood sugar. The high blood sugar is caused by either insulin secretion deficiency or dysfunction of biological action thereof or both. There are many methods for treatment of diabetes, including drug therapy, sports therapy, dietary therapy and so on. For the drug therapy, a therapeutic method of insulin injection is the most common and most effective therapeutic method, and this method requires a patient to inject insulin periodically and quantitatively. Therefore, injection pens become tools for patients to inject insulin by themselves.

The injection pen in the prior art comprises a liquid medication tube, a rotary tube, a clutch tube, a screw rod, and a nut rod. One end of the screw rod is provided with a plunger, wherein the plunger is provided inside the liquid medication tube. The other end of the screw rod is provided through the nut tube, the clutch tube is sleeved outside the nut tube, and the rotary tube is sleeved outside the clutch tube. When an injection dose needs to be adjusted, the rotary tube is rotated, and the rotary tube drives the clutch tube to move in an axial direction until to a desired position. After the adjustment is completed, the nut tube is rotated, and the nut tube drives the screw rod to move and push the plunger to move inside the liquid medication tube so as to perform injection. For each time of injection, a user performs quantitative injection by adjusting a position of the clutch tube.

However, regarding the injection pen in the prior art, since the user adjusts a scale value by adjusting the position of the clutch tube, after the injection of the liquid medication inside the liquid medication tube is completed, the user still can adjust the scale value by driving, by the rotary tube, the clutch tube to move it in the axial direction, but at this time, the user can no longer perform the injection, therefore, the adjustment of the scale value still can be performed for the injection pens in the prior art when the injection of the liquid medication inside the liquid medication tube is completed, thus the user cannot precisely know whether the injection of the liquid medication is completed.

SUMMARY

An object of the present disclosure is to provide a prefilled injection pen, so as to solve the technical problem existing in the prior art that the user cannot know precisely whether the injection of the liquid medication is completed.

The prefilled injection pen provided in the present disclosure comprises: a screw rod, a memory connection barrel, a fixed barrel, and a rotating barrel; on an end face of one end of the rotating barrel, a plurality of first one-way teeth are circumferentially provided in a uniform manner with an axis of the rotating barrel as a center; an opening at the end of the rotating barrel proximal to the first one-way teeth is an oblong hole (kidney-shaped hole, stadium-shaped hole); the memory connection barrel is provided inside the rotating barrel, and an inner wall of the memory connection barrel is provided with a protrusion cooperating (matching) with a thread of the screw rod; an end face of one end of the fixed barrel is provided with a ratchet pawl cooperating with the first one-way teeth, and the fixed barrel is provided thereon with a first internal (inner) thread cooperating with the screw rod; the screw rod is provided thereon with two machined plane surfaces opposite to each other in an extension direction of the screw rod, a plunger is provided at one end of the screw rod, and a stopper (block) is provided in a screw groove at the other end, wherein the stopper is configured to prevent the memory connection barrel from rotating relative to the screw rod.

Furthermore, the prefilled injection pen further comprises a fixed housing, a rotating barrel with scale, and a top-cap connection barrel; an outer wall of the fixed barrel is provided thereon with a first fixed protrusion; the fixed housing is a hollow housing open at two ends, an inner wall of the fixed housing is provided thereon with a second internal thread, and the inner wall of the other end is provided thereon with a first groove cooperating with the first fixed protrusion; an outer wall of the rotating barrel with scale is provided thereon with a first external thread cooperating with a second internal thread, and an inner wall of the rotating barrel with scale is provided thereon with a rotating protrusion; the top-cap connection barrel is provided inside the rotating barrel with scale, and an outer wall of the top-cap connection barrel is provided thereon with a second groove which is snap-connected with the rotating protrusion; an inner wall of the top-cap connection barrel is provided thereon with a sliding groove in an extension direction of the top-cap connection barrel; the memory connection barrel has one end which is away from the fixed barrel and provided with a sliding protrusion cooperating with the sliding groove.

Furthermore, the prefilled injection pen further comprises a top cap, a spring, a single-side one-way gear, and a double-side one-way gear with teeth on two sides intersecting with each other in inclined directions;

on an outer wall of the rotating barrel, a rotating strip is provided in an extension direction of the rotating barrel; the rotating barrel with scale has one end which is close to the fixed barrel and provided with an annular boss on an inner wall, and on the annular boss, a plurality of second one-way teeth are circumferentially provided in a uniform manner with an axis of the rotating barrel with scale as a center; the double-side one-way gear is sleeved on the rotating barrel, with one face thereof cooperating with the single-side one-way gear, and the other face cooperating with the second one-way teeth; an inner wall of the single-side one-way gear is provided thereon with third grooves cooperating with the rotating strip, the single-side one-way teeth has a face which is away from the double-side one-way teeth and abuts against one end of the top-cap connection barrel; an end face of the other end of the top-cap connection barrel is provided thereon with a connection disk, wherein one face of the connection disk away from the top-cap connection barrel is provided with a sleeve, and a circumferential face of the connection disk is provided thereon with a groove cooperating with the rotating protrusion; and the top cap is a hollow housing open at one end, and an inner end face of the top cap is provided thereon with a cylinder; the cylinder is provided inside the sleeve; the spring is sleeved outside the sleeve, with one end thereof abutting against the connection disk, and the other end abutting against the inner end face of the top cap.

Furthermore, the fixed housing comprises an outer barrel and a viewing barrel; an inner wall at one end of the outer barrel is provided thereon with a snapping groove, and the inner wall at the other end is provided thereon with a first groove, and the outer barrel is provided thereon with a viewing port; an outer wall at one end of the viewing barrel is provided thereon with a snapping protrusion cooperating with the snapping groove, the viewing barrel is provided with a notch at a position corresponding to the viewing port, the notch is in communication with the viewing port, and the viewing barrel is provided therein with the second internal thread.

Furthermore, an annular rotating portion open at two ends is provided at one end of the rotating barrel with scale, which is close to the top cap, wherein the annular rotating portion is sleeved outside the top cap, and a rotating protrusion is provided on an inner wall of the annular rotating portion.

Furthermore, an annular groove is provided on an outer wall of the top cap, a first annular protrusion is provided on an inner wall of the annular rotating portion, the first annular protrusion is provided inside the annular groove, and a gap is formed between the first annular protrusion and a side wall of the annular groove.

Furthermore, the prefilled injection pen further comprises a liquid medication cartridge and a needle; the liquid medication cartridge has one end which is open, and the other into which the needle is inserted, and the needle is in communication with the liquid medication cartridge; the plunger is provided inside the liquid medication cartridge, and a circumferential face of the plunger abuts against an inner wall of the liquid medication cartridge.

Furthermore, the prefilled injection pen further comprises a casing for the liquid medication cartridge; the outer barrel is provided with a second fixed protrusion on an inner wall at one end close to the fixed barrel; the casing for the liquid medication cartridge is open at two ends, the casing for the liquid medication cartridge is sleeved outside the liquid medication cartridge, and is provided with a fourth groove snap-fixed with the second fixed protrusion on an outer wall at one end close to the fixed barrel.

Furthermore, the casing for the liquid medication cartridge is provided with a second external thread on an outer wall at one end away from the fixed barrel; the needle comprises a needle body and a rotary barrel; the rotary barrel is open at one end, with an inner wall thereof being provided with a third internal thread cooperating with the second external thread; the needle body has one end inserted into a closed end of the rotary barrel, and is in communication with the liquid medication cartridge.

Furthermore, the prefilled injection pen further comprises a pen cap; the pen cap is a hollow housing open at one end, the pen cap is provided on an inner wall with a second annular protrusion; the casing for the liquid medication cartridge is provided on an outer wall with an annular groove which is snap-connected with the second annular protrusion.

During the use of the prefilled injection pen provided in the present disclosure, the user fixes the fixed barrel, and rotates the memory connection barrel clockwise for a certain number of turns. Since the first one-way teeth are locked with the ratchet pawl in the clockwise direction, the rotating barrel and the screw rod inside the rotating barrel are motionless, and the memory connection barrel moves a certain distance relative to the screw rod in the axial direction, thus the scale adjustment is completed. In injection, the user rotates the rotating barrel anticlockwise, and the rotating barrel drives the screw rod and the memory connection barrel on the screw rod to rotate. As the fixed barrel is motionless, the screw rod and the memory connection barrel rotate, and move a same distance relative to the fixed barrel in a direction opposite to the axial direction, and meanwhile the screw rod pushes the plunger to move, thereby achieving an injection of a certain dosage. When the prefilled injection pen is used next time, the user rotates the memory connection barrel clockwise again, and the memory connection barrel again moves a certain distance relative to the screw rod. When the liquid medication is depleted, the protrusion inside the memory connection barrel abuts against the stopper on the screw rod, and the stopper prevents the memory connection barrel from rotating relative to the screw rod, that is, at this time, the user is unable to rotate the memory connection barrel clockwise, thus notifying the user that the liquid medication has been depleted.

With the prefilled injection pen provided in the present disclosure, after the liquid medication is depleted, the user is no longer able to rotate the memory connection barrel clockwise to adjust the scale, thus the user can know that the liquid medication inside the injection pen is depleted.

BRIEF DESCRIPTION OF DRAWINGS

In order to more clearly illustrate technical solutions in embodiments of the present disclosure or in the prior art, accompanying drawings which are needed for description of the embodiments or the prior art will be introduced briefly below. Apparently, the accompanying drawings in the description below are merely for some embodiments of the present disclosure. A person ordinarily skilled in the art still can obtain other relevant drawings in light of these accompanying drawings, without paying inventive effort.

REFERENCE SIGNS

1—top cap; 2—spring; 3—top-cap connection barrel; 4—screw rod; 5—memory connection barrel; 6—single—side one-way gear; 7—double—side one-way gear; 8—rotating barrel with scale; 9—viewing barrel; 10—outer barrel; 11—rotating barrel; 12—fixed barrel; 13—plunger; 14—liquid medication cartridge; 15—casing for liquid medication cartridge; 16—pen cap; 17—rotating protrusion; 18—first one-way tooth; 19—ratchet pawl; 20—first fixed protrusion; 21—sliding protrusion; 22—sliding groove; 23—third groove; 24—first internal thread; 25—first external thread; 26—annular rotating portion; 27—rotating strip; 28—oblong hole; 29—stopper; 30—snapping protrusion; 31—notch; 32—snapping groove; 33—viewing port; 41—protrusion; 42—machined plane surface; 34—second one-way teeth.

DETAILED DESCRIPTION OF EMBODIMENTS

Technical solutions of the present disclosure will be described below clearly and comprehensively with reference to accompanying drawings. Apparently, the described embodiments are only a part of embodiments of the present disclosure, rather than all embodiments of the present disclosure. All other embodiments obtained by a person ordinarily skilled in the art based on the embodiments of the present disclosure without any inventive effort shall fall into the scope of protection of the present disclosure.

In the description of the present disclosure, it should be indicated that orientational or positional relations indicated by terms "center", "upper", "lower", "left", "right", "vertical", "horizontal", "inner", "outer" and so on are based on orientational or positional relations as shown in the accompanying drawings, merely for facilitating the description of the present disclosure and simplification of the description, rather than indicating or implying that related devices or elements have to be in the specific orientation or configured and operated in a specific orientation, therefore, they should not be construed as limiting the present disclosure. Besides, terms "first", "second", and "third" are merely for the purpose of description, but should not be construed as indicating or implying relative importance.

In the description of the present disclosure, it should be indicated that unless otherwise specified and defined explicitly, terms "install", "join", and "connect" should be construed in a broad sense. For example, it may be a fixed connection, a detachable connection, or an integral connection; it may be a mechanical connection, and also may be an electrical connection; it may be a direct connection, an indirect connection through via intermediate medium, or an inner communication between two elements. For a person ordinarily skilled in the art, specific meanings of the above-mentioned terms in the present disclosure may be understood according to specific circumstances.

Figure 1:
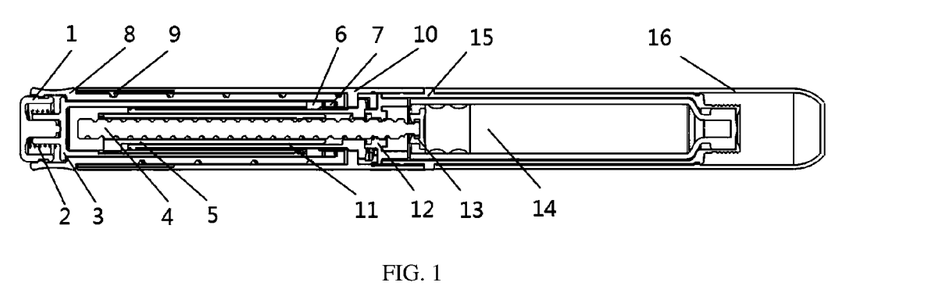
FIG. 1 is an assembling diagram of a prefilled injection pen provided in embodiments of the present disclosure.
Figure 2:
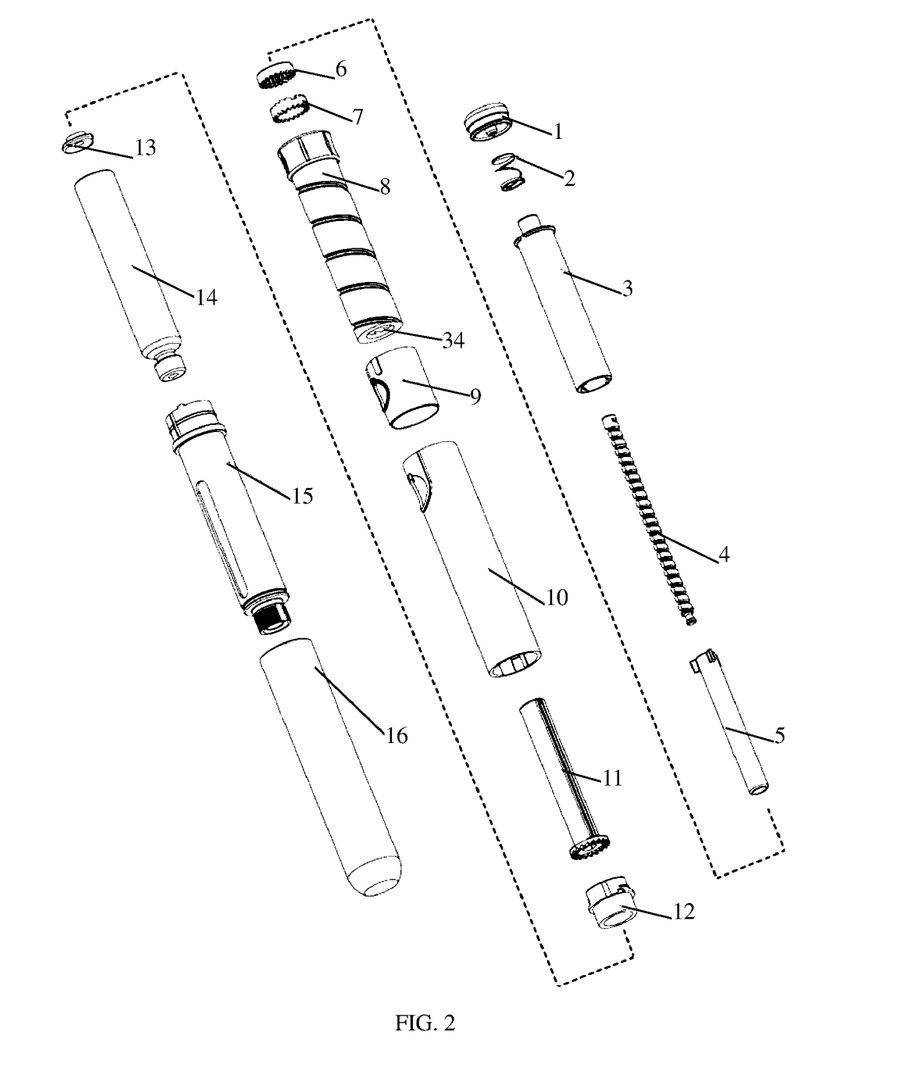
FIG. 2 is a structural schematic diagram of parts of the prefilled injection pen provided in embodiments of the present disclosure.
Figure 3:
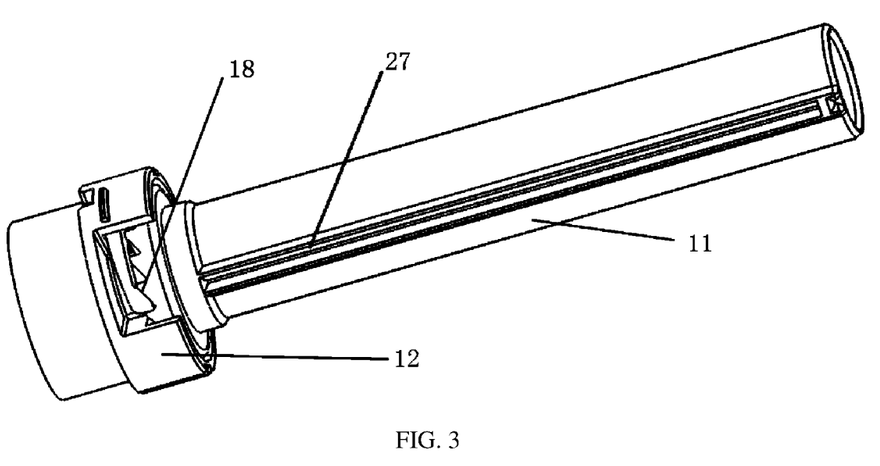
FIG. 3 is a structural schematic diagram illustrating cooperation between a rotating barrel and a fixed barrel in the prefilled injection pen provided in embodiments of the present disclosure.
Figure 4:
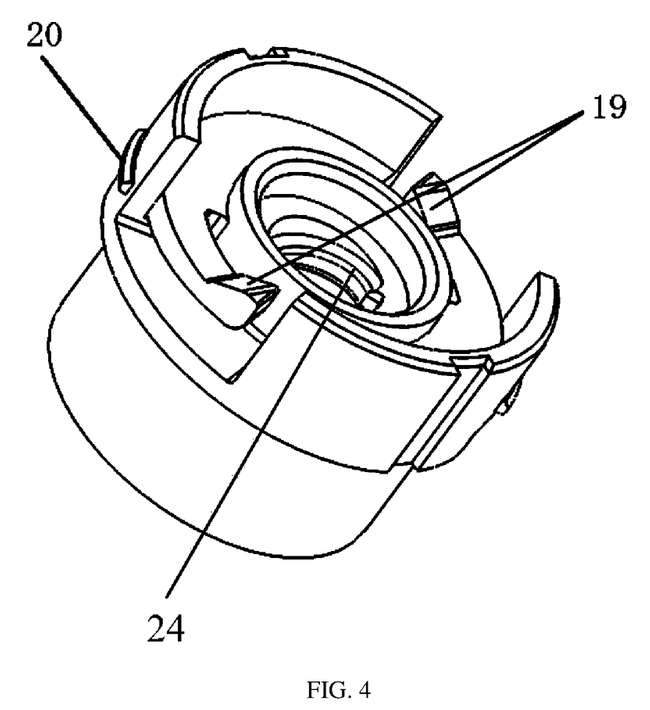
FIG. 4 is a structural schematic diagram of a fixed barrel in the prefilled injection pen provided in embodiments of the present disclosure.
Figure 5:
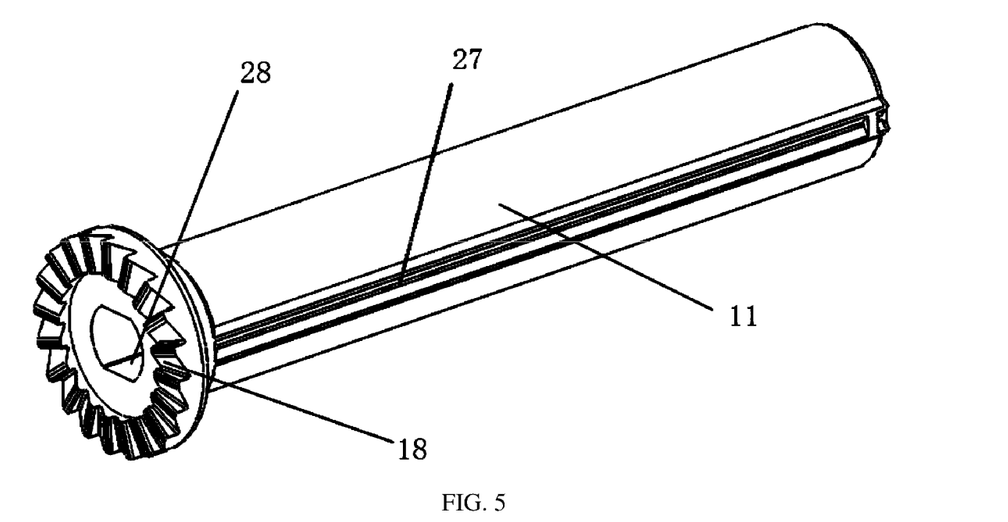
FIG. 5 is a structural schematic diagram of a rotating barrel in the prefilled injection pen provided in embodiments of the present disclosure.
Figure 6:
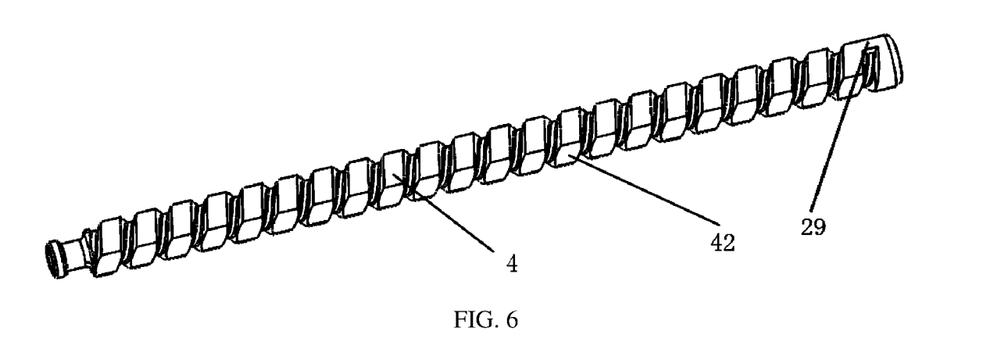
FIG. 6 is a structural schematic diagram of a screw rod in the prefilled injection pen provided in embodiments of the present disclosure.
Figure 7:
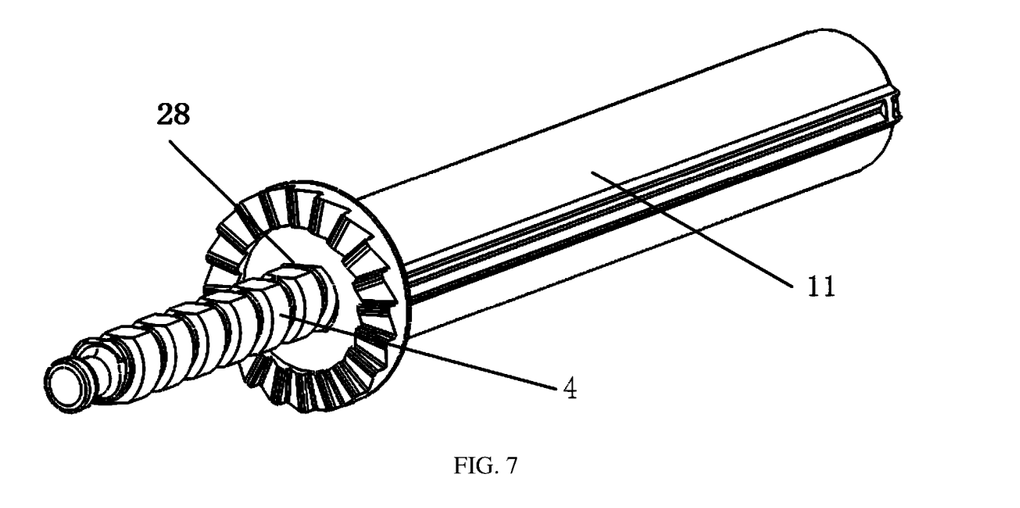
FIG. 7 is a structural schematic diagram illustrating cooperation between the rotating barrel and the screw rod in the prefilled injection pen provided in embodiments of the present disclosure.

FIG. 1 is a structural schematic diagram of a prefilled injection pen provided in embodiments of the present disclosure; FIG. 2 is a structural schematic diagram of parts of the prefilled injection pen provided in embodiments of the present disclosure; FIG. 3 is a structural schematic diagram illustrating cooperation between a rotating barrel and a fixed barrel in the prefilled injection pen provided in embodiments of the present disclosure; FIG. 4 is a structural schematic diagram of a fixed barrel in the prefilled injection pen provided in embodiments of the present disclosure; FIG. 5 is a structural schematic diagram of a rotating barrel in the prefilled injection pen provided in embodiments of the present disclosure; FIG. 6 is a structural schematic diagram of a screw rod in the prefilled injection pen provided in embodiments of the present disclosure; FIG. 7 is a structural schematic diagram illustrating cooperation between the rotating barrel and the screw rod in the prefilled injection pen provided in embodiments of the present disclosure. As illustrated in FIG. 1 to FIG. 7, a prefilled injection pen provided in the present embodiment comprises: a screw rod 4, a memory connection barrel 5, a fixed barrel 12, and a rotating barrel 11; on an end face of one end of the rotating barrel 11, a plurality of first one-way teeth 18 are circumferentially provided in a uniform manner with an axis of the rotating barrel 11 as a center; an opening at the end of the rotating barrel 11 is an oblong hole 28, with the end proximal to the first one-way teeth 18; the memory connection barrel 5 is provided inside the rotating barrel 11, and the memory connection barrel 5 is provided on an inner wall with a protrusion 41 cooperating with a thread of the screw rod 4; an end face of one end of the fixed barrel 12 is provided with a ratchet pawl 19 cooperating with the first one-way teeth 18, and the fixed barrel 12 is provided thereon with a first internal thread 24 cooperating with the screw rod 4; the screw rod 4 is provided thereon with two machined plane surfaces 42 opposite to each other in an extension direction of the screw rod 4, a plunger 13 is provided at one end of the screw rod 4, and a stopper 29 is provided in a thread groove at the other end, and the stopper 29 is configured to prevent the memory connection barrel 5 from rotating relative to the screw rod 4.

In the above, the two machined plane surfaces 42 of the screw rod 4 are parallel to a plane of the oblong hole 28, and the screw rod 4 may move inside the oblong hole 28 in an axial direction.

The number of the ratchet pawl 19 may one, and also may two or more. Preferably, the number of the ratchet pawl 19 is two, and the two ratchet pawls 19 are symmetrically provided on an end face of one end of the fixed barrel 12. With the cooperation between the two ratchet pawls 19 and the first one-way teeth 18, the first one-way teeth 18 may be more stable in a process of rotation.

During the use of the prefilled injection pen provided in the present disclosure, a user fixes the fixed barrel 12, and rotates the memory connection barrel 5 clockwise for a certain number of turns. Since the first one-way teeth 18 are locked with the ratchet pawl 19 in the clockwise direction, the rotating barrel 11 and the screw rod 4 inside the rotating barrel 11 are motionless, and the memory connection barrel 5 moves a certain distance relative to the screw rod 4 in the axial direction, thus the scale adjustment is completed. In injection, the user rotates the rotating barrel 11 anticlockwise. Since the first one-way teeth 18 are not locked with the ratchet pawl 19 in the anticlockwise direction, the rotating barrel 11 drives the screw rod 4 and the memory connection barrel 5 on the screw rod 4 to rotate. As the fixed barrel 12 is motionless, the screw rod 4 and the memory connection barrel 5 rotate, and move a same distance relative to the fixed barrel 12 in a direction opposite to the axial direction, and meanwhile the screw rod 4 pushes the plunger 13 to move, thereby achieving an injection of a certain dosage. When the prefilled injection pen is used next time, the user rotates the memory connection barrel 5 clockwise again, and the memory connection barrel 5 again moves a certain distance relative to the screw rod 4. When a liquid medication is depleted, the protrusion 41 inside the memory connection barrel 5 abuts against the stopper 29 on the screw rod 4, and the stopper 29 prevents the memory connection barrel 5 from rotating relative to the screw rod 4, that is, at this time, the user is unable to rotate the memory connection barrel 5 clockwise, thus notifying the user that the liquid medication has been depleted.

With the prefilled injection pen provided in the present disclosure, when the liquid medication is depleted, the user is unable to rotate the memory connection barrel 5 clockwise to adjust the scale, thus the user can know that the liquid medication inside the injection pen has been depleted.

Figure 8:
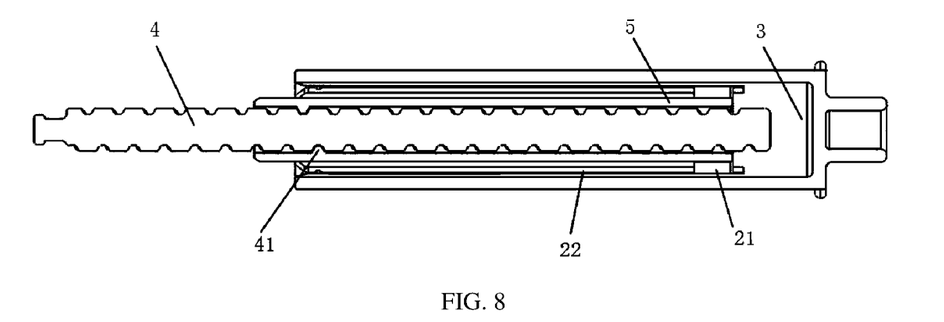
FIG. 8 is a structural schematic diagram of a top-cap connection barrel, a memory connection barrel, and the screw rod in the prefilled injection pen provided in embodiments of the present disclosure.
Figure 9:
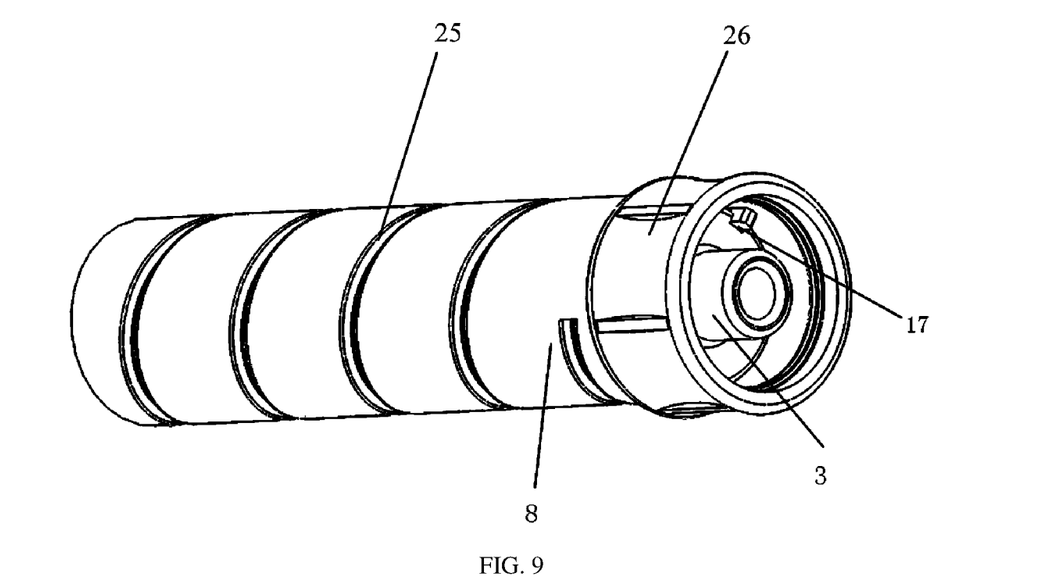
FIG. 9 is a structural schematic diagram of a rotating barrel with scale and the top-cap connection barrel in the prefilled injection pen provided in embodiments of the present disclosure.

FIG. 8 is a structural schematic diagram of the top-cap connection barrel, the memory connection barrel, and the screw rod in the prefilled injection pen provided in embodiments of the present disclosure; FIG. 9 is a structural schematic diagram of a rotating barrel with scale and the top-cap connection barrel in the prefilled injection pen provided in embodiments of the present disclosure. As illustrated in FIG. 1 to FIG. 9, on the basis of the above embodiments, furthermore, the prefilled injection pen further comprises a fixed housing, a rotating barrel with scale 8, and a top-cap connection barrel 3; an outer wall of the fixed barrel 12 is provided thereon with a first fixed protrusion 20; the fixed housing is a hollow housing open at two ends, an inner wall of the fixed housing is provided thereon with a second internal thread, and the inner wall of the other end is provided thereon with a first groove cooperating with the first fixed protrusion 20; an outer wall of the rotating barrel with scale 8 is provided thereon with a first external thread 25 cooperating with the second internal thread, and an inner wall of the rotating barrel with scale 8 is provided thereon with a rotating protrusion 17; the top-cap connection barrel 3 is provided inside the rotating barrel with scale 8, and an outer wall of the top-cap connection barrel 3 is provided thereon with a second groove which is snap-connected with the rotating protrusion 17; an inner wall of the top-cap connection barrel 3 is provided thereon with a sliding groove 22 in an extension direction of the top-cap connection barrel 3; the memory connection barrel 5 has one end which is away from the fixed barrel and provided with a sliding protrusion 21 cooperating with the sliding groove 22.

In the above, the first fixed protrusion 20 may be in multiple shapes, for example, a square shape, a circular shape, or an annular shape and so on.

The number of the first fixed protrusion 20 and the first groove each may be one, and also may be two or more, respectively.

In the present embodiment, during use, the user holds the fixed housing in hand, and rotates the rotating barrel with scale 8 clockwise. The fixed housing and the fixed barrel 12 are motionless. Since the rotating barrel with scale 8 and the fixed housing are in a threaded cooperation relation, the rotating barrel with scale 8 rotates relative to the fixed housing and moves a certain distance in the axial direction, meanwhile, the rotating barrel with scale 8 drives the top-cap connection barrel 3 to rotate and move in the axial direction, and the top-cap connection barrel 3 drives the memory connection barrel 5 to rotate relative to the screw rod 4 and move a certain distance in the axial direction, thus the scale adjustment is completed. The user rotates the rotating barrel 11 anticlockwise, thus the injection is completed.

In the present embodiment, by providing the fixed housing, the rotating barrel with scale 8, and the top-cap connection barrel 3, the user can realize the rotation of the memory connection barrel 5 relative to the screw rod 4 just by rotating the rotating barrel with scale 8, that is, the adjustment of the scale is achieved by the cooperation of the fixed housing, the rotating barrel with scale 8, and the top-cap connection barrel 3, whereby facilitating the user's use. Meanwhile, the fixed housing may protect the rotating barrel with scale 8 and the top-cap connection barrel 3 against dust, such that the parts of the injection pen may be kept clean.

Figure 10:
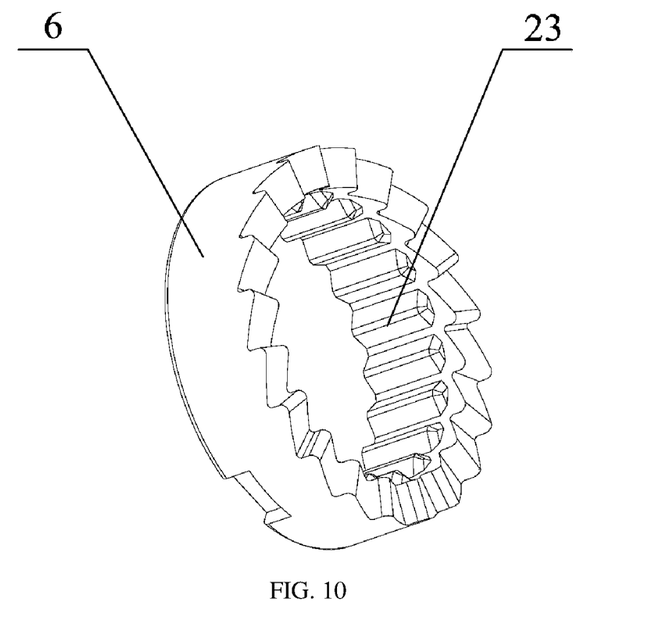
FIG. 10 is a structural schematic diagram of a single-side one-way gear in the prefilled injection pen provided in embodiments of the present disclosure.
Figure 11:
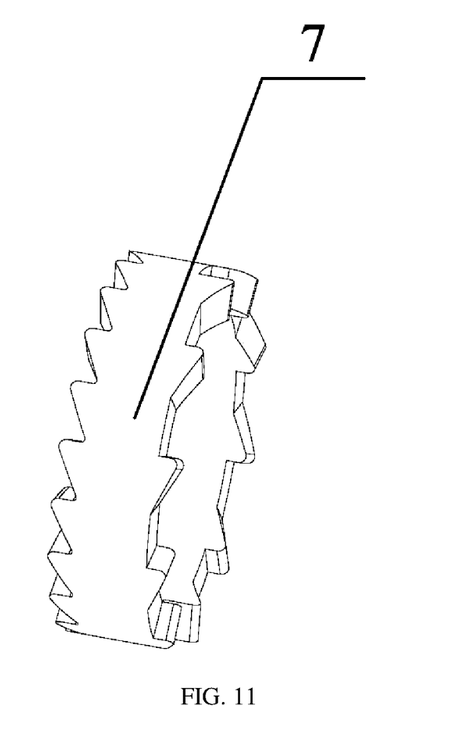
FIG. 11 is a structural schematic diagram of a double-side one-way gear in the prefilled injection pen provided in embodiments of the present disclosure.

FIG. 10 is a structural schematic diagram of a single-side one-way gear in the prefilled injection pen provided in embodiments of the present disclosure; FIG. 11 is a structural schematic diagram of a double-side one-way gear in the prefilled injection pen provided in embodiments of the present disclosure. As illustrated in FIG. 1 to FIG. 11, on the basis of the above embodiments, furthermore, the prefilled injection pen further comprises a top cap 1, a spring 2, a single-side one-way gear 6, a double-side one-way gear 7 with teeth on two sides intersecting with each other in inclined directions; on an outer wall of the rotating barrel 11, a rotating strip 27 is provided in an extension direction of the rotating barrel 11; the rotating barrel with scale 8 has one end which is close to the fixed barrel 12 and provided with an annular boss on an inner wall, wherein on the annular boss, a plurality of second one-way teeth 34 (referring to FIG. 2 and FIG. 14) are circumferentially provided in a uniform manner with an axis of the rotating barrel with scale 8 as a center; the double-side one-way gear 7 is sleeved on the rotating barrel 11, with one face thereof cooperating with the single-side one-way gear 6, and the other face cooperating with the second one-way teeth 34; the single-side one-way gear 6 is provided on an inner wall with third grooves 23 cooperating with the rotating strip 27, the single-side one-way teeth has a face which is away from the double-side one-way teeth and abuts against one end of the top-cap connection barrel 3; an end face of the other end of the top-cap connection barrel 3 is provided thereon with a connection disk, wherein one face of the connection disk away from the top-cap connection barrel 3 is provided with a sleeve, and a circumferential face of the connection disk is provided thereon with a groove cooperating with the rotating protrusion 17; the top cap 1 is a hollow housing open at one end, and the top cap 1 is provided on an inner end face with a cylinder; the cylinder is provided inside the sleeve; the spring 2 is sleeved outside the sleeve, with one end thereof abutting against the connection disk, and the other end abutting against the inner end face of the top cap 1.

In the above, the double-side one-way gear 7 is a hollow housing open at two ends, and on end faces of two ends thereof, a plurality of one-way teeth are circumferentially provided in a uniform manner with an axis of the double-side one-way gear 7 as a center, and the one-way teeth on the end faces of the two ends intersect with each other in inclined directions.

The single-side one-way gear 6 is a hollow housing open at two ends, and on an end face of an end thereof, a plurality of one-way teeth are circumferentially provided in a uniform manner with an axis of the single-side one-way gear 6 as a center.

Figure 14:
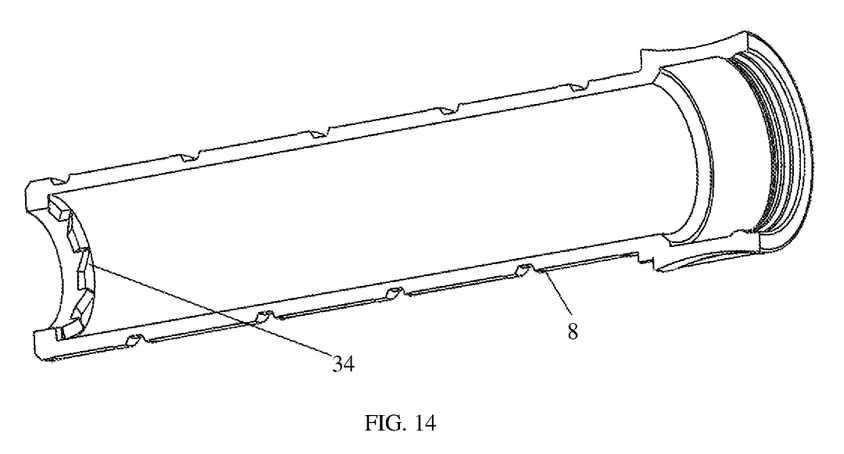
FIG. 14 is a structural schematic diagram of a second one-way teeth of the rotating barrel with scale in the prefilled injection pen provided in embodiments of the present disclosure.

In the present embodiment, during use, the user holds the fixed housing in hand, and rotates the rotating barrel with scale 8 clockwise, then the rotating barrel with scale 8 rotates and moves in the axial direction, meanwhile, the rotating barrel with scale 8 drives the top-cap connection barrel 3 to rotate, and the top-cap connection barrel 3 drives the memory connection barrel 5 to rotate and move in the axial direction. Since the second one-way teeth 34 and the teeth of the double-side one-way gear 7 are in an unlocked state, the teeth of the double-side one-way gear 7 and of the single-side one-way gear 6 are in a locked state, and meanwhile, the single-side one-way gear 6 and the rotating barrel 11 have a cooperation of the rotating strip 27 and the third grooves 23, the double-side one-way gear 7 and the single-side one-way gear 6 simultaneously move in the axial direction without rotation, and meanwhile push the top-cap connection barrel 3 to move in the axial direction. When tooth skipping occurs between the double-side one-way gear 7 and the second one-way teeth 34, the spring 2 is compressed, after the tooth skipping between the double-side one-way gear 7 and the second one-way teeth 34, the spring 2 stretches to recover to an original state, such that the spring 2 is repeatedly compressed and stretches when the user rotates the rotating barrel with scale 8.

During injection, the user presses the top cap 1 downwards, such that the top-cap connection barrel 3, the double-side one-way gear 7, and the single-side one-way gear 6 have no gap, thereby there is no bouncing space for the spring 2, and the tooth skipping can hardly take place between the second one-way teeth 34 and the double-side one-way teeth. At this time, the user rotates the rotating barrel with scale 8 anticlockwise, the rotating barrel with scale 8 drives the single-side one-way gear 6 to rotate by the double-side one-way gear 7, the single-side one-way gear 6 drives the rotating barrel 11 to rotate, and the rotating barrel 11 drives the screw rod 4 to rotate and move in a direction opposite to the axial direction. Meanwhile, the rotating barrel with scale 8 drives the top-cap connection barrel 3 to rotate and move in the direction opposite to the axial direction, and the top-cap connection barrel 3 drives the memory connection barrel 5 to rotate and move in the direction opposite to the axial direction. Since the screw rod 4 and the memory connection barrel 5 have a same angular velocity at this time, the screw rod 4 and the memory connection barrel 5 simultaneously rotate and move in the direction opposite to the axial direction, and the screw rod 4 pushes the plunger 13 to move, thus the injection is completed.

In the present embodiment, the double-side one-way gear 7 and the single-side one-way gear 6 are provided on the rotating barrel 11, and the user may complete the adjustment of the scale and the injection of the liquid medication just by rotating the rotating barrel with scale 8, thus the operation is convenient. Moreover, the skipping of the teeth between the double-side one-way gear 7 and the second one-way teeth 34 can facilitate the user in controlling strength of rotation when rotating the rotating barrel with scale 8, thereby facilitating the scale adjustment.

Figure 12:
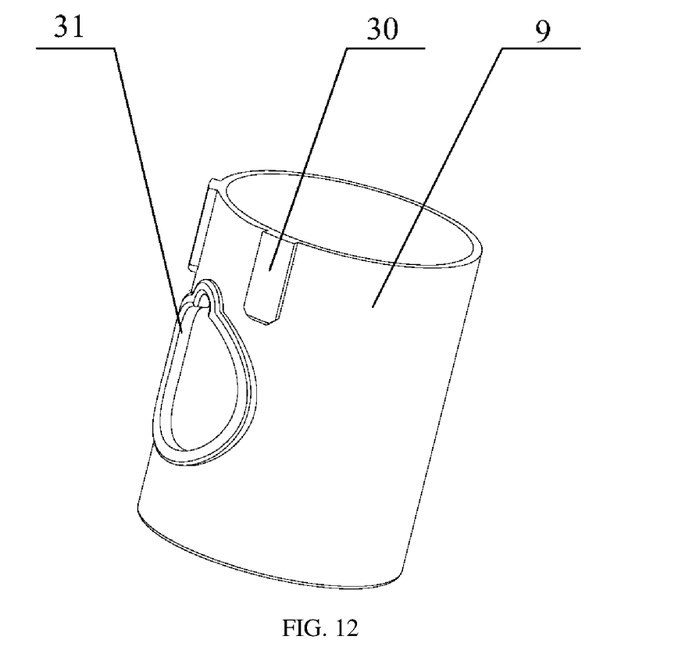
FIG. 12 is a structural schematic diagram of a viewing barrel in the prefilled injection pen provided in embodiments of the present disclosure.
Figure 13:
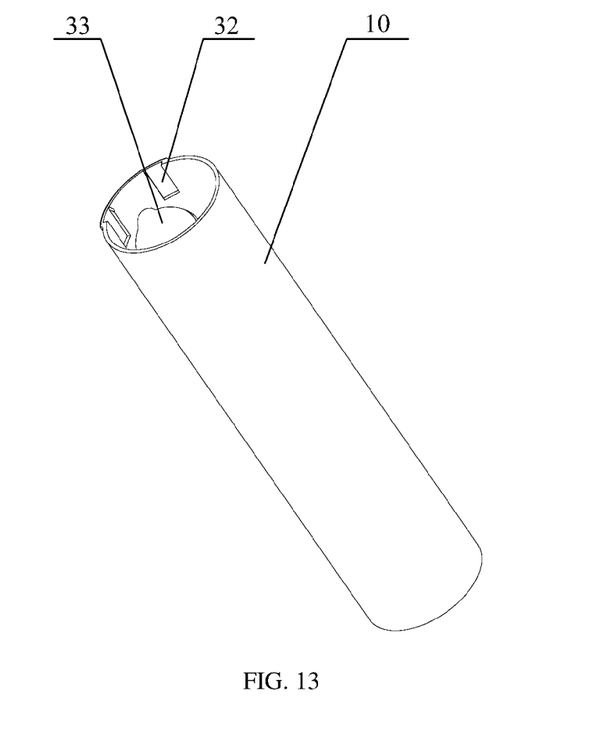
FIG. 13 is a structural schematic diagram of an outer barrel in the prefilled injection pen provided in embodiments of the present disclosure.

FIG. 12 is a structural schematic diagram of a viewing barrel in the prefilled injection pen provided in embodiments of the present disclosure; FIG. 13 is a structural schematic diagram of an outer barrel in the prefilled injection pen provided in embodiments of the present disclosure. As illustrated in FIG. 1, FIG. 2, FIG. 12, and FIG. 13, on the basis of the above embodiments, furthermore, the fixed housing comprises an outer barrel 10 and a viewing barrel 9; an inner wall at one end of the outer barrel 10 is provided thereon with a snapping groove 32, and provided with a first groove on the inner wall at the other end, and the outer barrel 10 is provided thereon with a viewing port 33; an outer wall at one end of the viewing barrel 9 is provided thereon with a snapping protrusion 30 cooperating with the snapping groove 32, the viewing barrel 9 is provided with a notch 31 at a position corresponding to the viewing port 33, wherein the notch 31 is in communication with the viewing port 33, and the viewing barrel 9 is provided therein with the second internal thread.

In the present embodiment, the fixed housing is provided as the outer barrel 10 and the viewing barrel 9, and the viewing port 33 is provided on the outer barrel 10, and the notch 31 is provided on the viewing barrel 9. Such provision facilitates the user in viewing a distance of movement of the rotating barrel with scale 8, that is, such provision facilitates viewing a scale numerical value.

As illustrated in FIG. 9, on the basis of the above embodiments, furthermore, an annular rotating portion 26 open at two ends is provided at one end of the rotating barrel with scale 8, which is close to the top cap 1. The annular rotating portion 26 is sleeved outside the top cap 1. A rotating protrusion 17 is provided on an inner wall of the annular rotating portion 26.

In the above, a plurality of protrusions may be provided on an outer wall of the annular rotating portion 26, such that a friction force between a hand of the user and the annular rotating portion 26 may be increased when the user holds the annular rotating portion 26 in hand to rotate, thus facilitating the user in rotating.

In the present embodiment, by providing the annular rotating portion 26 on the rotating barrel with scale 8, during use, the user can rotate the rotating barrel with scale 8 just by rotating the annular rotating portion 26, thus facilitating the user's operation.

As illustrated in FIG. 1 and FIG. 2, on the basis of the above embodiments, furthermore, an annular groove is provided on an outer wall of the top cap 1, a first annular protrusion is provided on an inner wall of the annular rotating portion 26, wherein the first annular protrusion is provided inside the annular groove, and a gap is formed between the first annular protrusion and a side wall of the annular groove.

In the present embodiment, when the skipping of teeth occurs between the second one-way teeth 34 and the double-side one-way teeth, the top-cap connection barrel 3 moves in the axial direction, the annular groove moves relative to the first annular protrusion, and the spring 2 is compressed. After the skipping of teeth between the second one-way teeth 34 and the double-side one-way teeth, the annular groove moves relative to the first annular protrusion in an opposite direction, and the spring 2 stretches.

In the present embodiment, by the cooperation between the first annular protrusion and the annular groove, relative displacement of the top-cap connection barrel 3 relative to the rotating barrel with scale 8 is defined, thus the structure is simple, and the operation is convenient.

As illustrated in FIG. 1 and FIG. 2, on the basis of the above embodiments, furthermore, the prefilled injection pen further comprises a liquid medication cartridge 14 and a needle; the liquid medication cartridge 14 is open at one end, and is inserted with the needle at the other end, and the needle is in communication with the liquid medication cartridge 14; the plunger 13 is provided inside the liquid medication cartridge 14, and a circumferential face of the plunger 13 abuts against an inner wall of the liquid medication cartridge 14.

In the present embodiment, the user rotates the rotating barrel with scale 8 clockwise to adjust the scale, then presses the top cap 1 downwards, and rotates the rotating barrel with scale 8 anticlockwise, then the plunger 13 moves and pushes the liquid medication to be injected into a human body through the needle.

In the present embodiment, the liquid medication cartridge 14 and the needle cooperate with each other to complete the injection, which is simple in structure, and convenient for processing and manufacturing.

As illustrated in FIG. 1 and FIG. 2, on the basis of the above embodiments, furthermore, the prefilled injection pen further comprises a casing 15 for the liquid medication cartridge; the outer barrel 10 is provided with a second fixed protrusion on an inner wall at one end close to the fixed barrel 12; the casing 15 for liquid medication cartridge is open at two ends, the casing 15 for the liquid medication cartridge is sleeved outside the liquid medication cartridge 14, and is provided with a fourth groove snap-fixed with the second fixed protrusion on an outer wall at one end close to the fixed barrel 12.

In the present embodiment, the casing 15 for the liquid medication cartridge is provided outside the liquid medication cartridge 14, and the casing 15 for the liquid medication cartridge may serve a protective function for the liquid medication cartridge 14, thus preventing the liquid medication cartridge 14 from being damaged when being impacted by an external force, and thereby prolonging the service life of the injection pen.

As illustrated in FIG. 1 and FIG. 2, on the basis of the above embodiments, furthermore, the casing 15 for the liquid medication cartridge is provided with a second external thread on an outer wall at one end away from the fixed barrel 12. The needle comprises a needle body and a rotary barrel; the rotary barrel is open at one end, with an inner wall thereof being provided with a third internal thread cooperating with the second external thread; the needle body has one end inserted into a closed end of the rotary barrel, and is in communication with the liquid medication cartridge 14.

In the present embodiment, the rotary barrel and the casing 15 for the liquid medication cartridge are detachable by a threaded connection therebetween, thus facilitating the user in fitting the needle.

As illustrated in FIG. 1 and FIG. 2, on the basis of the above embodiments, furthermore, the prefilled injection pen further comprises a pen cap 16; the pen cap 16 is a hollow housing open at one end, the pen cap 16 is provided on an inner wall with a second annular protrusion; the casing for the liquid medication cartridge is provided on an outer wall with an annular groove which is snap-connected with the second annular protrusion.

In the present embodiment, during use, the user pulls out the pen cap 16 from the casing for the liquid medication cartridge, rotates the rotating barrel with scale 8 clockwise to adjust the scale, then presses down the top cap 1, and rotates the rotating barrel with scale 8 anticlockwise, thus the injection is completed.

In the present embodiment, when not using the injection pen, the user sleeves the pen cap 16 outside the casing for the liquid medication cartridge, which may protect the needle against dust and other impurities, ensuring the cleanliness of the injection pen when being used.

Finally, it should be indicated that the various embodiments above are merely used to illustrate the technical solutions of the present disclosure, rather than limiting the present disclosure. Although the detailed description is made to the present disclosure with reference to the above-mentioned embodiments, those ordinarily skilled in the art should understand that the technical solutions recited in the above-mentioned embodiments still can be modified, or equivalent substitutions can be made to some or all of the technical features therein; these modifications or substitutions do not make the corresponding technical solutions essentially depart from the scope of the technical solutions of the embodiments of the present disclosure.

What is claimed is:

1. A prefilled injection pen, comprising: a screw rod, a memory connection barrel, a fixed barrel, and a rotating barrel, wherein on an end face of one end of the rotating barrel, a plurality of first one-way teeth are circumferentially provided in a uniform manner with an axis of the rotating barrel as a center; an opening at the one end of the rotating barrel is an oblong hole; the memory connection barrel is provided inside the rotating barrel, and an inner wall of the memory connection barrel is provided thereon with a protrusion cooperating with a thread of the screw rod; an end face of one end of the fixed barrel is provided with a ratchet pawl cooperating with the plurality of first one-way teeth, and the fixed barrel is provided thereon with a first internal thread cooperating with the screw rod; and the screw rod is provided thereon with two machined plane surfaces opposite to each other in an extension direction of the screw rod, a plunger is provided at one end of the screw rod, and a stopper is provided in a thread groove at another end of the screw rod, and the stopper is configured to prevent the memory connection barrel from rotating relative to the screw rod.

2. The prefilled injection pen according to claim 1, wherein the prefilled injection pen further comprises a fixed housing, a rotating barrel with scale, and a top-cap connection barrel;

an outer wall of the fixed barrel is provided thereon with a first fixed protrusion; the fixed housing is a hollow housing open at two ends, an inner wall of the fixed housing is provided thereon with a second internal thread, and one end of the inner wall of the fixed housing is provided thereon with a first groove cooperating with the first fixed protrusion; an outer wall of the rotating barrel with scale is provided thereon with a first external thread cooperating with the second internal thread of the inner wall of the fixed housing, and an inner wall of the rotating barrel with scale is provided thereon with a rotating protrusion; the top-cap connection barrel is provided inside the rotating barrel with scale, and an outer wall of the top-cap connection barrel is provided thereon with a second groove which is snap-connected with the rotating protrusion; an inner wall of the top-cap connection barrel is provided thereon with a sliding groove in an extension direction of the top-cap connection barrel; and the memory connection barrel has one end which is distal to the fixed barrel and provided with a sliding protrusion cooperating with the sliding groove.

3. The prefilled injection pen according to claim 2, wherein the prefilled injection pen further comprises a top cap, a spring, a single-side one-way gear, and a double-side one-way gear;

on an outer wall of the rotating barrel, a rotating strip is provided in an extension direction of the rotating barrel; the rotating barrel with scale has one end which is proximal to the fixed barrel and provided with an annular boss on the inner wall of the rotating barrel with scale, and on the annular boss, a plurality of second one-way teeth are circumferentially provided in a uniform manner with an axis of the rotating barrel with scale as a center; the double-side one-way gear is sleeved on the rotating barrel, with one face of the double-side one-way gear cooperating with the single-side one-way gear, and the other face of the double-side one-way gear cooperating with the plurality of second one-way teeth; an inner wall of the single-side one-way gear is provided thereon with third grooves cooperating with the rotating strip, the single-side one-way gear has a face which is distal to the double-side one-way gear and abuts against one end of the top-cap connection barrel; an end face of the other end of the top-cap connection barrel is provided thereon with a connection disk, one face of the connection disk distal to the top-cap connection barrel is provided with a sleeve, and a circumferential face of the connection disk is provided thereon with a groove cooperating with the rotating protrusion; and the top cap is a hollow housing open at one end, and an inner end face of the top cap is provided thereon with a cylinder; the cylinder is provided inside the sleeve; the spring is sleeved outside the sleeve, with one end of the spring abutting against the connection disk, and another end of the spring abutting against the inner end face of the top cap.

4. The prefilled injection pen according to claim 3, wherein the fixed housing comprises an outer barrel and a viewing barrel;

an inner wall at one end of the outer barrel is provided thereon with a snapping groove, and the inner wall at another end of the outer barrel is provided with the first groove, the outer barrel is provided thereon with a viewing port; an outer wall at one end of the viewing barrel is provided thereon with a snapping protrusion cooperating with the snapping groove, the viewing barrel is provided with a notch at a position corresponding to the viewing port, the notch is in communication with the viewing port, and the viewing barrel is provided therein with the second internal thread.

5. The prefilled injection pen according to claim 4, wherein an annular rotating portion open at two ends is provided at one end of the rotating barrel with scale, which is proximal to the top cap; the annular rotating portion is sleeved outside the top cap; and the rotating protrusion is provided on an inner wall of the annular rotating portion.

6. The prefilled injection pen according to claim 5, wherein an annular groove is provided on an outer wall of the top cap, a first annular protrusion is provided on the inner wall of the annular rotating portion, the first annular protrusion is provided inside the annular groove, and a gap is formed between the first annular protrusion and a side wall of the annular groove.

7. The prefilled injection pen according to claim 1, wherein the prefilled injection pen further comprises a liquid medication cartridge and a casing for the liquid medication cartridge;

an inner wall at one end of an outer barrel proximal to the fixed barrel is provided thereon with a second fixed protrusion; the casing for the liquid medication cartridge is open at two ends, the casing for the liquid medication cartridge is sleeved outside the liquid medication cartridge, and is provided with a fourth groove which is snap-fixed with the second fixed protrusion on an outer wall at the one end of the outer barrel.

8. The prefilled injection pen according to claim 7, wherein the prefilled injection pen further comprises a pen cap;

the pen cap is a hollow housing open at one end, an inner wall of the pen cap is provided thereon with a second annular protrusion; an outer wall of the casing for the liquid medication cartridge is provided thereon with an annular groove which is snap-connected with the second annular protrusion.

\* \* \* \* \*